US008810197B2

(12) United States Patent
Juergens

(10) Patent No.: US 8,810,197 B2
(45) Date of Patent: Aug. 19, 2014

(54) AUTOCLAVABLE CHARGING DEVICE FOR A RECHARGEABLE ENERGY STORE OF A SURGICAL INSTRUMENT AND ASSOCIATED METHOD

(75) Inventor: Thorsten Juergens, Hamburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 309 days.

(21) Appl. No.: 13/256,344

(22) PCT Filed: Feb. 4, 2010

(86) PCT No.: PCT/EP2010/000699
§ 371 (c)(1),
(2), (4) Date: Sep. 13, 2011

(87) PCT Pub. No.: WO2010/127729
PCT Pub. Date: Nov. 11, 2010

(65) Prior Publication Data
US 2012/0007550 A1    Jan. 12, 2012

(30) Foreign Application Priority Data
Mar. 16, 2009  (DE) .......................... 10 2009 013 034

(51) Int. Cl.
*H02J 7/00* (2006.01)

(52) U.S. Cl.
USPC .......................................................... 320/108

(58) Field of Classification Search
USPC .......................................................... 320/108
See application file for complete search history.

(56) References Cited

U.S. PATENT DOCUMENTS

| 6,666,875 B1 * | 12/2003 | Sakurai et al. ................ 606/169 |
| 6,847,190 B2 * | 1/2005 | Schaefer et al. .............. 320/107 |

(Continued)

FOREIGN PATENT DOCUMENTS

| DE | 33 17 531 A1 | 11/1983 |
| DE | 10 2006 043 145 A1 | 3/2008 |

(Continued)

*Primary Examiner* — Arun Williams
(74) *Attorney, Agent, or Firm* — Scully, Scott, Murphy & Presser, P.C.

(57) ABSTRACT

The invention relates to an autoclavable charging device (12, 13, 15-20) for an electrical and rechargeable energy store (30) of a surgical instrument (11). The invention further relates to a method for charging a rechargeable energy store (30) in an autoclaved surgical instrument (11) or for an autoclaved surgical instrument (11).

Figure 1:
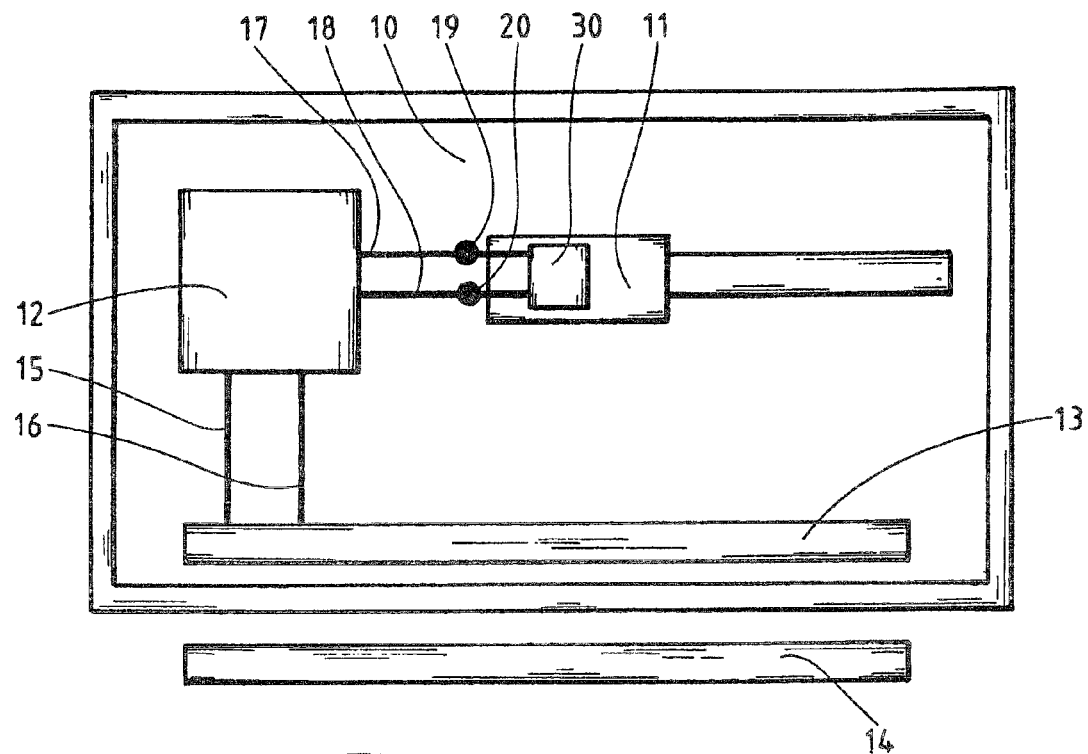

The charging device according to the invention is characterized in that this device comprises a receiving device (13) for receiving and converting an electromagnetic field into an alternating current voltage, and comprising charging electronics (12) galvanically connected to the receiving device (13), wherein the charging electronics (12) convert the alternating current voltage into the charging voltage, and wherein the charging device (12, 13, 15-20) comprises at least one galvanic output connection (17, 18, 19, 20) for galvanically connecting to the energy store (30) of the surgical instrument (11).

The method according to the invention is characterized in that before charging the energy store (30) is galvanically connected to the at least one galvanic output connection (17-20) of the charging device (12, 13, 15-20), wherein the surgical instrument (11) and/or the energy store (30) is then autoclaved, wherein the surgical instrument (11) and/or the energy store (30) is then brought into an effective range of a device (14) generating an electromagnetic field, and a resonant coupling is generated between the device (14) generating the electromagnetic field and a receiving device (13) of the charging device (12, 13, 15-20), said coupling leading to an energy transfer from the device (14) generating the electromagnetic field to the receiving device (13), wherein the energy is used at least partially for generating a charging voltage for the energy store (30).

13 Claims, 1 Drawing Sheet

(56) References Cited

U.S. PATENT DOCUMENTS

| | | | |
|---|---|---|---|
| 2003/0160590 A1* | 8/2003 | Schaefer et al. | 320/107 |
| 2007/0182367 A1* | 8/2007 | Partovi | 320/108 |
| 2009/0096413 A1* | 4/2009 | Partovi et al. | 320/108 |

FOREIGN PATENT DOCUMENTS

| | | |
|---|---|---|
| EP | 1 684 396 A2 | 7/2006 |
| EP | 1 481 692 B1 | 3/2007 |
| EP | 1 868 275 A2 | 12/2007 |
| EP | 2 031 731 A1 | 3/2009 |
| JP | 61-222450 A | 10/1986 |
| JP | 2000-287987 A | 10/2000 |
| JP | 2001-251611 A | 9/2001 |
| JP | 2001-255835 A | 9/2001 |
| JP | 2005-348941 A | 12/2005 |
| JP | 2006-314181 A | 11/2006 |
| JP | 2008-67590 A | 3/2008 |
| WO | WO 02/28301 A1 | 4/2002 |
| WO | WO 2007/008646 A2 | 1/2007 |
| WO | WO 2008/017041 A2 | 2/2008 |
| WO | WO 2008/118178 A1 | 10/2008 |

* cited by examiner

AUTOCLAVABLE CHARGING DEVICE FOR A RECHARGEABLE ENERGY STORE OF A SURGICAL INSTRUMENT AND ASSOCIATED METHOD

CROSS-REFERENCE TO RELATED APPLICATIONS

This application claims priority to PCT Application EP2010/000699 filed on Feb. 4, 2010, which claims priority to Application No. DE 10 2009 013 034.9 filed on Mar. 16, 2009, the contents of each of which are incorporated herein by reference.

The invention relates to an autoclavable charging device for a rechargeable energy store of a surgical instrument. The invention further relates to a method for charging a rechargeable energy store in an autoclaved surgical instrument or for an autoclaved surgical instrument.

Surgical instruments, such as endoscopes or laparoscopes for instance, are frequently used multiple times. The instruments are autoclaved in an autoclave for guaranteeing multiple uses and providing a sterile surgical instrument. An autoclave is a pressure vessel that can be sealed in a gas-tight manner that is used for heat treating the surgical instrument in an overpressure range. For autoclaving, the air in the autoclave can be removed by repeated evacuation alternating with an inflow of steam and subsequent inflow of high temperature steam, at over 130° C. for example, with an overpressure of 3 bar for example. Alternatively, the air in the autoclave can also be displaced by saturated steam. Different steps are performed in autoclaves for autoclaving, and thereby sterilizing the surgical instruments.

An appropriate autoclave and a corresponding method for operating the autoclave are described in the document EP 1 481 692 B1, where in that document, the autoclave is called a sterilizer, in particular. An autoclave method is described in EP 1 481 692 B1 with reference to the FIGS. 1a) to 3, for example.

Applicable surgical instruments frequently have electrical actuators or lighting means and electronics, which are supplied with an energy source. The energy source is typically outside of the surgical instruments, such that cables are necessary for connecting to the surgical instrument. As an alternative to this, an energy source is provided in the surgical instrument, for example a rechargeable energy source, such as a battery, or an energy source is provided that is exchangeably fastened to or in the surgical instrument.

This presents the problem that charged batteries substantially discharge during autoclaving, so that they are possibly completely emptied during the operation. In that case, the operation can no longer continue, which must be avoided. An alternative would be to charge the energy store of the surgical instruments after the autoclaving. For this purpose, however, the sterility of the surgical instruments is no longer maintained, which is undesirable.

For autoclaving, the surgical instrument is typically placed in a carrier device, and the carrier device with the surgical instrument is wrapped in a cloth. As soon as the cloth is opened, the sterility is not maintained.

The object of the present invention is to provide a possibility to charge a rechargeable energy store in a surgical instrument, which is autoclaved, or a rechargeable energy store that has been autoclaved for a surgical instrument, while maintaining the sterility of the surgical instrument or the energy store.

This objective is solved by an autoclavable charging device for an electrical and rechargeable energy store of a surgical instrument, where the charging device comprises a receiving device for receiving an electromagnetic field and for converting the field into an alternating current voltage and a charging electronics galvanically connected to the receiving device, where the charging electronics convert the alternating current voltage into a charging voltage and, where the charging device has at least one galvanic outlet connection for a galvanic connection to the energy store of the surgical instrument.

By providing such an autoclavable charging device according to the invention, it is possible to recharge electrical and rechargeable energy stores that are autoclaved while maintaining the sterility.

Thereby it is possible during the operation to exchange electrical and rechargeable energy stores that are detachably fastened at or in a surgical instrument when their energy has run low. As a result, an operation can be performed to completion while maintaining sterility.

The receiving device preferably comprises a first resonator device.

Further preferably the charging electronics are adapted to charge a rechargeable energy store, in the surgical instrument in particular, that is galvanically connected to the charging electronics.

According to the invention, an autoclavable carrying device with an integrated autoclavable charging device, which was described above according to the invention, is provided for an electrical and rechargeable energy store, in particular an accumulator, disposed in a surgical instrument.

The objective is solved by an autoclavable charging device for a surgical instrument, where the carrying device has a charging device for an electrical and rechargeable energy store, in particular an accumulator, disposed in the surgical instrument, where the charging device comprises a receiving device for receiving an electromagnetic field and converting the field into an alternating current voltage, and charging electronics galvanically connected to the receiving device, where the charging electronics convert the alternating current voltage into a charging voltage, and where the charging device has at least one galvanic output connection for galvanically connecting to the surgical instrument.

An autoclavable carrying device constructed in this manner provides a very efficient possibility for recharging the energy store in the surgical instrument, even after the instrument was autoclaved, without influencing the sterility. In the process, the towel wrapped around the autoclavable carrying device and the surgical instrument need not be removed because the energy necessary for charging the rechargeable energy store is transferred without cables. Thus, the autoclavable carrying device has the receiving device necessary for receiving the energy, and charging electronics as well as a galvanic output connection to which the surgical instrument can be connected.

When placing the surgical instruments on the autoclavable carrying device, the instrument is connected to the galvanic output connection or the galvanic outlet connections of the charging electronics. The sterilization cloth is then wrapped around the carrying device and the surgical instrument. The autoclaving then takes place.

After autoclaving, the carrying device, in particular the receiving device, is placed in the vicinity of a transmitting device disposed in particular at a settable distance to the carrying device, or the vicinity of a device generating an electromagnetic field, and corresponding energy that is transmitted from the transmitting device, is absorbed by the receiving device and converted using the charging electronics into a charging voltage, that is conducted via the galvanic connection to the surgical instrument. Within the scope of the invention, the term transmitting device is also used instead of a device generating an electromagnetic field. In this context, these are both the same device.

Preferably, a plug connection is provided for the galvanic connection. It is possible that only one plug connection is provided and the other electrical contact or galvanic contact occurs via the ground of the carrying device and the housing of the surgical instrument. For this purpose, the housing of the surgical instrument must be composed at least partially of a conductive material, and furthermore the autoclavable carrying device must also be composed at least partially of a conductive material.

Preferably the receiving device comprises a first resonator device. The resonator device is preferably tunable, that is, the resonance frequency can be tuned. Preferably a coil, which is provided with or without a ferromagnetic material, is provided in the resonator device.

Preferably the charging electronics are adapted for charging a rechargeable energy store in a surgical instrument that is galvanically connected to the charging electronics. The charging electronics can be typical charging electronics, for instance those available everywhere, for charging accumulators. However, they must be adapted to the value of the alternating current voltage which is provided by the receiving device. A typical charging device is described for example in DE 33 17 531 A1.

It is particularly preferable if the carrying device has a receiving region that at least in sections has a compatible shape and/or is adapted in shape to at least a section of the surgical instrument. The receiving area then has at least in sections a contour that is adapted at least to a section of the surgical instrument. As a result a secure galvanic connection is possible between the output connection or connections and the surgical instrument. Clamps, in which the surgical instrument can be clamped, that are elastically attached to the carrying device, can also be used for this purpose.

Preferably an arrangement of an autoclavable charging device according to the invention and/or an autoclavable carrying device according to the invention is provided with a device, which is coupled to the receiving device via a provided path, transmitting or generating an electromagnetic field. Within the scope of the invention, arrangement is understood to also mean a combination in particular.

The device generating an electromagnetic field preferably has a second resonator device. The second resonator device is preferably also tunable and, preferably has a coil. The coil can be provided with a ferromagnetic material.

It is particularly preferable if the arrangement of the second resonator device is in resonance with the first resonator device. Through this measure a particularly efficient contact-less transmission of energy is possible. This is preferably a resonant coupling of the two resonator devices which is preferably understood to be a transforming magnet arrangement. The defined distance or the specified path between the resonator devices is, as mentioned, contact-less, i.e. galvanically contact-less and extends through the air, the sterilization cloth and possibly further elements of the carrying device.

The cordless energy transmission can be an inductive energy transmission. However, preferably there is a resonant coupling of the first and the second resonator device so that a very efficient energy transmission with a high degree of efficiency is possible. For this purpose, reference is made to the documents WO 2007/008646 A2 and WO 2008/118 178 A1, in which this type of wireless, non-radiating energy transmission is described. The energy transmission takes place here via a coupling of the resonance fields of the first and second resonator device. This can function over several centimeters or even up to several meters, where in the scope of the invention a distance of 5 cm to 20 cm is preferred between the first and second resonator device.

Within the scope of the invention, generating and receiving an electromagnetic field also means the coupling of second resonator devices, in particular the resonance coupling of these two resonator devices. The term electromagnetic field correspondingly also comprises an electromagnetic radiation. With this, the device generating the electric field is also a device transmitting an electric radiation, and the receiving device can correspondingly receive and convert an electromagnetic field or receive and convert an electromagnetic radiation.

The disclosed content of WO 2007/008646 A2 and WO 2008/118178 A1 should be incorporated in the entirety of their disclosed content into this patent application, at least insofar as the technology relates to the contact-less transmission of energy.

The objective is further solved by a method for charging a rechargeable energy store in an autoclaved surgical instrument, where before the charging the surgical instrument is placed on a carrying device according to the invention and is galvanically connected to the at least one galvanic output connection of the charging device, where the carrying device with the surgical instrument is then autoclaved, where the carrying device with the surgical instrument is then brought into an effective range of a device transmitting or generating an electromagnetic field, and where a resonance coupling is created between the device generating the electromagnetic field and a receiving device of the charging device, which leads to an energy transfer from the device generating the electromagnetic field to the receiving device, where the energy is used at least to some extent for generating a charging voltage for the energy store.

Within the scope of the invention, the term of the device generating an electromagnetic field also comprises a device transmitting an electromagnetic field.

For autoclaving, the surgical instrument and the carrying device are wrapped in a cloth that can be sterilized. The method according to the invention for charging the rechargeable energy store preferably occurs in a state in which after the autoclaving the surgical instrument, the cloth is still wrapped around the carrying device and the surgical instrument.

The objective is further solved by a method for charging a rechargeable energy store in an autoclaved surgical instrument or for an autoclaved surgical instrument, where before the charging the energy store is galvanically connected to the at least one galvanic output connection of the charging device according to one of the claims 1 to 3, where the surgical device and/or the energy store is then autoclaved, in particular together with the charging device, where the surgical device and/or the energy store, in particular together with the charging device, is then brought into an effective range of a device transmitting an electromagnetic field, and a resonant coupling is created between the device generating the electromagnetic field and a receiving device of the charging device, which leads to an energy transmission from the device generating the electromagnetic field to the receiving device, where the energy is used at least to some extent for generating a charging voltage for the energy store.

Before the charging, the surgical instrument is preferably placed on a carrying device according to the invention, where the surgical instrument which has the energy store is galvanically connected to the at least one galvanic output connection of the charging device, where the carrying device is then autoclaved with the surgical instrument and, where the carrying device with the surgical instrument is then brought into an effective range of the device transmitting the electro-magnetic field.

Figure 2:
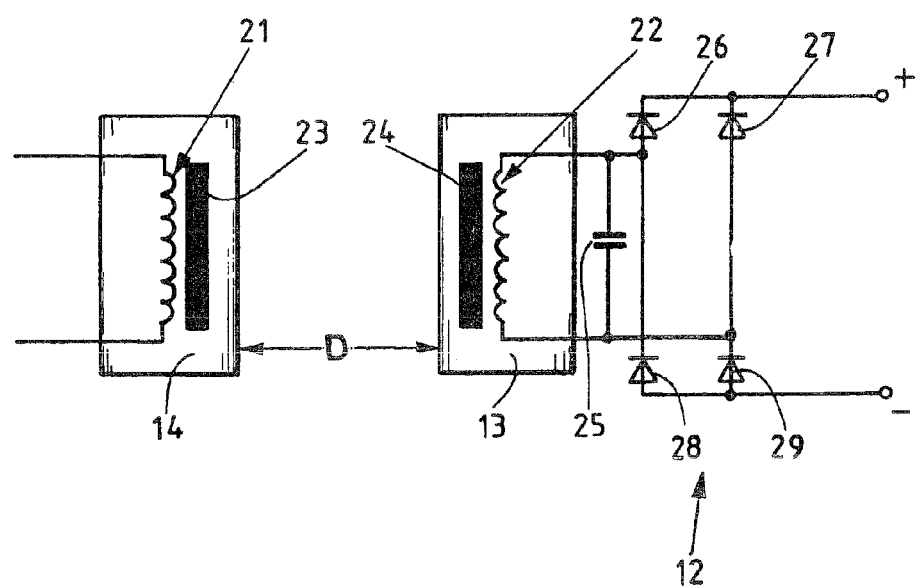

The invention is described below, without restricting the general idea of the invention, using exemplary embodiments with reference to the drawings, whereby we expressly refer to the drawings with regard to the disclosure of all details according to the invention that are not explained in greater detail in the text. They show:

FIG. 1 a schematic top view of an autoclavable carrying device according to the invention, and FIG. 2 a schematic representation of a part of an arrangement according to the invention.

In the following figures, the same or similar types of elements or corresponding parts have the same reference numbers so that a corresponding re-introduction can be omitted.

FIG. 1 shows a schematic top view of a carrying device 10 according to the invention that is bordered by a wall which is indicated schematically by the respectively parallel lines at the edge of the carrying device 10. A first resonance device 13 is disposed on the carrying device 10, and in particular fixed detachably on the carrying device 10. The first resonance device 13 has two galvanic or electrical connections 15 and 16 to charging electronics 12 that are designed, in particular to be able to charge an accumulator 30. Two electrical connections 17, 18 go from the charging electronics 12 via plug contacts 19, 20 to the galvanic connection with the accumulator 30 in the surgical instrument 11. The accumulator 30 is used for example to drive an actuator, not shown, in the surgical instrument, such as a saw or forceps, for instance. Further, the accumulator 30 can also be used to supply a photo chip or a camera with voltage, or to provide a light source with voltage.

FIG. 1 further shows a second resonator device 14 disposed at a distance from the carrying device 10. The second resonator device 14 generates an electromagnetic field that is in resonance with the first resonator device 13, such that an efficient energy transmission occurs from the second resonator device 14 to the first resonator device 13. As a result, an alternating charging voltage is available, via the electrical connection 15 and 16, to the charging electronics 12 that is then converted into a charging voltage available, via the electrical connections 17 and 18, at the plug contacts 19, 20. The components of the first resonator device 13, of the electrical connections 15, 16, of the charging electronics 12, of the electrical connections 17, 18 and of the plug contacts 19, 20 are preferably rigidly connected, or detachably connectable, to the carrying device 10. Correspondingly, the surgical instrument 11 can be removed from the carrying device and subsequently used, and even in a cordless manner.

FIG. 2 shows a part of a schematic arrangement according to the invention. The second resonator device 14 has a coil 21 and a ferromagnetic material 23. A first resonator device 13 as the device which receives the energy is disposed at a distance D to the second resonator device 14. The first resonator device 13 is disposed on a carrying device, not shown.

The first resonator device 13 also has a coil 22 and a ferromagnetic material 24. It is not essential for the ferromagnetic material 24 to be present. A capacitor 25 can also belong to the first resonator device 13. Correspondingly, the second resonator device 14 can also have a capacitor, which is not shown. Because the wires that are used in the resonator devices already have a capacitance, a further capacitor is not absolutely necessary. Nevertheless a further capacitor simplifies the tunability of the respective resonator devices. The coils 21 and 22 can preferably be tuned by their inductance, thus can be changed.

In FIG. 2, charging electronics 12 that are electrically connected to the first resonator device 13 are shown only in a very simplified variant, namely consisting of four diodes 26-29, which generate a type of direct current voltage from the available alternating current voltage.

Thus, the invention relates to cordless energy transmission by means of two electrical coils for example, that are coupled via a resonant frequency. As a result, the efficiency is significantly increased in comparison to a conventional inductive transmission of energy. Hereby, a great deal of energy can be transmitted, where as a result accumulators can be charged to a high capacity in a short period of time. It is possible to use cordless endoscopes or other surgical instruments that require an energy supply. Due to the invention it is possible to charge such a surgical instrument while preserving sterility. Likewise, accumulator-driven light sources can also be charged. It is particularly advantageous to provide a charging electronics separately from the surgical instrument so that the surgical instrument can be constructed to be small and lightweight.

Thus, the solution according to the invention integrates the corresponding devices for the energy transmission and the devices providing the charging voltage on the autoclavable carrying device, which is also referred to as a Steri-Tray. Sufficient construction space is provided there in order to integrate a large-scale coil, and corresponding space to house further charging electronics.

The transmitted energy is converted into a charging current or into a charging voltage which can charge the surgical instrument located on the carrying device. The surgical instrument placed on the carrying device is then charged via a galvanic connection to the charging device in the carrying device. Thus, it is possible that it is not necessary to remove the surgical instrument from the sterile packaging. Therefore the surgical instrument remains sterile.

The coils can be used with or without ferrite cores depending on the application case. The resonance circuit preferably oscillates in the megahertz range. Thus, a typical frequency can be provided between 5 MHz and 400 MHz for example. The frequency used is preferably in a frequency range that is compatible with an operating room.

Alternatively, it is possible, but not shown in the drawings, to first autoclave and then appropriately charge exchangeable, rechargeable energy stores such as accumulators in an autoclavable charging device in order to use these as exchangeable accumulators for operations, and before starting the operation to have a sterile operator connect the appropriately sterilized, autoclaved accumulators to an autoclaved surgical instrument, in order to then provide this surgical instrument appropriately with energy through the thusly sterilized or autoclaved accumulator.

All named features, including those taken from the drawings alone, and individual features, which are disclosed in combination with other features, are considered individually and in combination as essential to the invention. Embodiments according to the invention can be satisfied through individual characteristics or a combination of several characteristics.

LIST OF REFERENCES 10 carrying device
11 surgical instrument
12 charging electronics
13 first resonator device
14 second resonator device
15 electrical connection
17 electrical connection 18 electrical connection
19 plug contact
20 plug contact
21 coil
22 coil
23 ferromagnetic material
24 ferromagnetic material
25 capacitor
26 diode
27 diode
28 diode
29 diode
30 accumulator
D distance

The invention claimed is:

1. An autoclavable charging device for an electrical and rechargeable energy store for a surgical instrument, the charging device comprising:
   an enclosure having an autoclavable interior,
   a receiving device disposed in the interior of the enclosure for receiving an electromagnetic field from a device located outside the enclosure, the receiving device being positioned at a predetermined distance from the device such that the receiving device converts the electromagnetic field from the device into an alternating current voltage,
   charging electronics disposed in the interior of the enclosure, the charging electronics being galvanically connected to the receiving device, wherein the charging electronics convert the alternating current voltage into a charging voltage, and
   at least one galvanic output connection disposed in the interior of the enclosure for galvanically connecting the charging electronics to the energy store for the surgical instrument.

2. The autoclavable charging device according to claim 1, wherein the receiving device comprises a first resonator device.

3. The autoclavable charging device according to claim 2, wherein the energy store is a rechargeable energy store and the charging electronics are adapted to charge the rechargeable energy store galvanically connected to the charging electronics.

4. The autoclavable charging device according to claim 1, wherein the energy store is a rechargeable energy store and the charging electronics are adapted to charge the rechargeable energy store galvanically connected to the charging electronics.

5. The autoclavable charging device according to claim 1, wherein the enclosure is a carrying device having a receiving region which at least in sections has a compatible shape and/or is adapted in shape to at least one section of the surgical instrument.

6. An autoclavable charging system comprising:
   the autoclavable charging device according to claim 1, and
   the device generating the electromagnetic field, wherein the receiving device is positioned at a predetermined distance from the device.

7. The autoclavable charging system according to claim 6, wherein the receiving device comprises a first resonator device and the device generating the electromagnetic field comprises a second resonator device.

8. The autoclavable charging system according to claim 7, wherein the second resonator device is in resonance with the first resonator device.

9. The autoclavable charging system according to claim 6, wherein the energy store is an accumulator.

10. The autoclavable charging device according to claim 1, wherein the energy store is an accumulator.

11. A method for charging a rechargeable energy store in an autoclaved surgical instrument or for an autoclaved surgical instrument, the method comprising:
   configuring an autoclavable charging device to include an enclosure having an autoclavable interior; a receiving device disposed in the interior of the enclosure for receiving an electromagnetic field from a device located outside the enclosure; charging electronics disposed in the interior of the enclosure, the charging electronics being galvanically connected to the receiving device, and at least one galvanic output connection disposed in the interior of the enclosure for galvanically connecting the charging electronics to the energy store for the surgical instrument;
   before charging, inserting one of the surgical instrument having the energy store or the energy store in the interior of the enclosure and galvanically connecting the energy store to the at least one galvanic output connection of the charging device;
   autoclaving the surgical instrument and/or the energy store while the energy store is contained within the enclosure,
   while the surgical instrument and/or energy store is contained within the enclosure, bringing the receiving device into an effective range of the device generating the electromagnetic field to generate a resonant coupling between the device generating the electromagnetic field and the receiving device of the charging device, said coupling resulting in an energy transfer from the device generating the electromagnetic field to the receiving device, and
   at least partially transferring the energy from the receiving device to the energy store to charge the energy store.

12. The method according to claim 9, wherein enclosure is a carrying device.

13. The method of claim 11, wherein the receiving device converts the received electromagnetic field from the device to an alternating current voltage and the charging electronics converts the alternating current voltage to the energy provided to the energy store.

* * * * *